United States Patent [19]

Gispen

[11] Patent Number: 4,550,099
[45] Date of Patent: Oct. 29, 1985

[54] PEPTIDES WITH NERVE-REGENERATING PROPERTIES

[75] Inventor: Willem H. Gispen, Zeist, Netherlands

[73] Assignee: Akzo N.V., Arnhem, Netherlands

[21] Appl. No.: 658,544

[22] Filed: Oct. 9, 1984

Related U.S. Application Data

[63] Continuation of Ser. No. 425,087, Sep. 21, 1982, abandoned.

[30] Foreign Application Priority Data

Apr. 8, 1981 [NL] Netherlands .......................... 8101724

[51] Int. Cl.$^4$ .............................................. A61K 37/00
[52] U.S. Cl. ........................................ 514/14; 514/16; 514/17
[58] Field of Search ................. 260/112.5 R; 424/177; 514/14, 16, 17

[56] References Cited

U.S. PATENT DOCUMENTS

| | | | |
|---|---|---|---|
| 3,842,064 | 10/1974 | Greven .......................... | 260/112.5 R |
| 3,850,904 | 11/1974 | Greven .......................... | 260/112.5 R |
| 4,104,371 | 8/1978 | Greven et al. ................ | 260/112.5 R |
| 4,110,322 | 8/1978 | Greven et al. ................ | 360/112.5 R |

FOREIGN PATENT DOCUMENTS 2,328,453  10/1975  France .......................... 260/112.5 R

OTHER PUBLICATIONS

European Journal of Pharm. 76, (1981), 73-79.
Recueil, Journal of the Royal Netherlands Chem. Soc. 98, (1979), 168-172.

*Primary Examiner*—Delbert R. Phillips
*Attorney, Agent, or Firm*—Abelman Frayne Rezac & Schwab

[57] ABSTRACT

The present invention relates to the use of the peptides of the general formula:

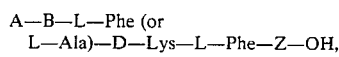

A—B—L—Phe (or
    L—Ala)—D—Lys—L—Phe—Z—OH,     I where
A represents one of the following groups: H—L—Met, H—L—Met(O), H—L—Met(O$_2$), desamino-Met, desamino-Met(O) or desamino-Met(O$_2$),
B represents one of the following di-peptide fragments: Glu—His or Ala—Ala, where one amino acid residue of this di-peptide fragment can occur in the D form, and
Z is either absent, or represents the amino acid residue Gly, or is the peptide fragment (10-16)—ACTH, where the amino acid L—Lys may be replaced, if desired, by D—Lys at position 11 of the (10-16-)—ACTH fragment, and the functional derivatives thereof in promoting axonal regeneration.

4 Claims, No Drawings

PEPTIDES WITH NERVE-REGENERATING PROPERTIES

This is a continuation of application Ser. No. 425,087 filed Sept. 21, 1982 now abandoned.

The present invention relates to the use of certain peptides as means of promoting axonal regeneration.

Injuries to the nerve fibres generally cause a degeneration of the nerve section which may extend far beyond the damage. This so-called Wallerian degeneration may lead eventually to complete desensitising of the target organ. The substances transported by axons prepared in the perikaryon collect at the site of the nerve damage where they cause a swelling.

After a delay of approximately three days, new branches occur at the site of the nerve damage or swelling. These branches grow at a speed of approximately 3 to 4 mm a day, making use of still intact basal layers of tissue of the degenerated nerve until complete recovery of the degenerated nerve system concerned is achieved.

Surprisingly, it has now been found that by administering certain peptides which are not a component or fragment of proteins or peptides occuring in the body, this natural process of axonal regeneration can be appreciably stimulated and promoted, so that a complete recovery of the degenerated nerve system concerned is possible within a significantly shorter period of time.

These peptides can be represented by the general formula I:

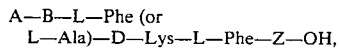

A—B—L—Phe (or
L—Ala)—D—Lys—L—Phe—Z—OH,   I where
A represents one of the following groups: H—L—Met, H—L—Met(O), H—L—Met($O_2$), desamino-Met, desamino-Met(O) or desamino-Met($O_2$),
B represents one of the following di-peptide fragments: Glu—His or Ala—Ala, where one amino acid residue of this di-peptide fragment can occur in the D form, and
Z is either absent, or represents the amino acid residue Gly, or is the peptide fragment (10–16)—ACTH, where the amino acid L—Lys may be replaced, if desired, by D—Lys at position 11 of the (10–16-)—ACTH fragment, and the functional derivatives thereof.

Functional derivatives in this case means:
(a) C-terminal aliphatic esters (1–6 C atoms), such as the methyl, ethyl, propyl, isopropyl, butyl or isobutyl ester,
(b) C-terminal amides or mono-methyl or dimethyl-substituted amides,
(c) pharmaceutically acceptable acid addition salts, and
(d) metal complexes obtained by contacting the peptide concerned with a poorly soluble salt, hydroxide or oxide of a metal, preferably zinc.

The latter peptide-metal complexes cause a slow release in the body of the peptide from the complex, so that a prolonged activity of the peptide is achieved.

The above peptides of formula I and their functional derivatives are known as psycho-pharmacological peptides and more particularly as peptides which delay the extinction of conditioned (avoidance) behaviour. These peptides are described in the U.S. Pat. Nos. 3.842.064, 4.110.322 and 4.104.371.

As already briefly indicated above, the peptides in question stimulate the regeneration of nerves degenerated by injury, so that these peptides are excellently suited for administering to patients who, through injuries and the resulting degeneration of a specific section of the nervous system, cannot make use, or can do so only partly, of the sensory-motor or muscular functions "served" by this degenerated nerve system.

In particular, this could apply to patients who have undergone operative surgery, victims of road accidents, or patients who suffer from symptoms of frost bite.

However, nerves are not damaged merely by mechanical injury, but other causes, such as addiction to alcohol, poisoning, overdosage of drugs, etc. can cause damage to the nerve tissue. The peptides in question can also be used in these cases.

Within the framework of the present invention, specially suitable peptides are the peptides of formula I, where
A represents H—L—Met, H—L—Met(O) or H—L—Met($O_2$) and more particularly H—L—Met(O) and H—L—Met($O_2$),
B represents one of the following di-peptide fragments: L—Glu—L—His, L—Glu—D—His or L—Ala—L—Ala, and
Z is absent or represents the peptide fragment with the sequence 10–16 ACTH, where the amino acid Lys at position 11 may, if desired, occur in the D-form, and the functional derivatives thereof.

More particularly, preference is given to the use of the peptide: H—L—Met($O_2$)—L—Glu—L—His—L—Phe—D—Lys—L—Phe—OH or a functional derivative thereof and, in the case of s/c application, the zinc complex thereof.

A particular advantage of using the peptides in question is, further, that they can be taken orally. In general, most (lengthier) peptides can be taken only by an injection (suppository) or intra-nasally (by nose spray). The dosages in which the peptides can be administered for this new application varies between 0.1 μg and 10 mg per kg of body weight per day.

The peptides in question were tested in an experimental animal model. In Albino Wistar Rats of the female sex (130–150 g body weight), the right sciatic nerve was exposed by cleaving the overlying muscles. The exposed nerve bundle was then crushed with a hemostatic forceps 6 mm distal to the sciatic notch for 30 seconds prior to closure and suturing of the wound. Immediately after this operation (which took place under narcosis, hypnorm, 0.08 ml/mg body weight), the rats were injected subcutaneously with the peptide to be tested or with placebo, this being repeated every 48 hours. Control rats were subjected to a sham operation, in which the sciatic nerve was exposed but not damaged, and were subsequently treated subcutaneously with placebo (vehicle). These subcutaneous injections were given in the skin fold of the rats' necks.

Total recovery of the damage and the resulting nerve regeneration was measured by means of a test of the sensori-motor function of the right leg of the rat by comparison with the left.

During this test, immediately before the next injection, the sole of the foot was exposed every 48 hours to a hot air stream of 47° C., for a maximum of 3 seconds. Thus, the results of the test were obtained by determining whether the rat retracted its right foot within this 3-second period (yes/no criterion). During this period, the left foot was withdrawn in each case (in general within 1–1.5 sec.).

Furthermore, histological sections were made of the tibial nerve at various distances from the nerve damage and at various times after the damage was caused. The newly formed, myelinated axons in the regenerating nerve were visualised by colour and their numbers quantified.

In both tests, administration of the peptides in question in a dosage of 1 and 10 μg/per rat per 48 hours significantly accelerated the recovery of a degenerated nerve system in comparison with a placebo treatment. For example, the peptide H—L—Met(O$_2$)—L—Glu—L—His—L—Phe—D—Lys—L—Phe—OH administered subcutaneously,
(a) dissolved in a physiological salt solution, or
(b) as a zinc phosphate-peptide suspension (isotonic with a physiological salt solution and with a pH 7–8)

stimulates the recovery of the sensori-motor function in a dosage of 1 μg/rat per 48 hours at an average of 10%, and with a dosage of 10 μg/rat per 48 hours at an average of 15%.

EXAMPLES

1. A suspension for injection consists of

| | | |
|---|---|---|
| 30 μg | H—Met(O$_2$)—Glu—Hio—Phe—D-Lys—Phe—OH | |
| 1.5 mg | zinc | |
| 0.63 mg | Na$_2$HPO$_4$.2H$_2$O | |
| 3.5 mg | NaCl | |
| 10 mg | benzylalcohol. | |

2. A 100 mg tablet consists of

| | | |
|---|---|---|
| 7.5 mg | H—Met(O$_2$)—Glu—His—Phe—D-Lys—Phe—OH | |
| 1 mg | talc | |
| 0.5 mg | magnesium stearate | |
| 2.5 mg | carboxy methyl cellulose | |
| 20 mg | starch | |
| 68.5 mg | lactose. | |

3. A similar tablet was prepared containing

| | |
|---|---|
| 7.5 mg | H—Met(O$_2$)—D-Lys—Phe—Gly—D-Lys—Pro—Val—Gly—Lys—Lys—OH. |

4. Hard gelatine capsule containing

| | |
|---|---|
| 22.3 mg | H—Met(O$_2$)—Glu—His—Phe—D-Lys—Phe—OH |
| 153.4 mg | mannitol |
| 7.4 mg | povidone |
| 1.8 mg | magnesiumstearate. |

I claim:

1. A method of treating patients suffering from a partly degenerated nerve system which comprises treating said patients with an effective amount of a peptide of the formula I A—B—L—Phe(or
 L—Ala)—D—Lys—L—Phe—Z—OH.    (I)

wherein

A represents one of the following groups:
H—L—Met, H—L—Met(O), H—L—Met(O$_2$), desamino-Met, desamino-Met(O), or desamino-Met(O$_2$), B represents one of the following di-peptide fragments: L—Glu—L—His, D—Glu—L—His, L—Glu—D—His, L—Ala—L—Ala, D—Ala—L—Ala or L—Ala—D—Ala, and Z represents a single bond, the amino acid residue Gly, or the peptide residue Gly—L—Lys—L—Pro—L—Val—Gly—L Lys—L—Lys or Gly—D—Lys—L—Pro—L—Val—Gly—L—Lys—L—Lys, or a functional derivative selected from a C-terminal C$_1$-C$_6$ aliphatic ester, a C-terminal unsubstituted, monomethyl or dimethyl substituted amide, a pharmaceutically acceptable acid addition salt, or a metal complex thereof, said amount being effective in stimulating or promoting axonal regeneration.

2. A method according to claim 1 wherein an effective amount of a compound of the formula H—L—Met(O$_2$)—L—GIU—L—His—L—Phe—D—Lys—L—Phe—OH or a functional derivative thereof as defined in claim 1, is administered.

3. A method according to claim 1 for treating patients suffering from a partially degenerated peripheral nerve system which comprises treating said patients with an effective amount of a peptide of formula I or a functional derivative or salt or metal complex thereof, as defined in claim 1.

4. A method according to claim 1 for treating patients suffering from a partially degenerated central nerve system which comprises treating said patients with an effective amount of a peptide of formula I or a functional derivative or salt or metal complex thereof, as defined in claim 1.

* * * * *